(12) United States Patent
Hembre

(10) Patent No.: US 6,448,430 B1
(45) Date of Patent: *Sep. 10, 2002

(54) PROCESS FOR THE PREPARATION OF ARYL CARBOXYLATE ESTERS

(75) Inventor: Robert Thomas Hembre, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/524,242

(22) Filed: Mar. 13, 2000

Related U.S. Application Data

(60) Provisional application No. 60/153,071, filed on Sep. 10, 1999.

(51) Int. Cl.⁷ .......................... C07C 67/14; C07C 69/00
(52) U.S. Cl. ........................................ 560/98; 560/130
(58) Field of Search .................... 560/130, 98

(56) References Cited

U.S. PATENT DOCUMENTS

| | | | |
|---|---|---|---|
| 2,082,790 A | * 6/1937 | Cherry | ....................... 260/99.4 |
| 3,772,389 A | 11/1973 | Lowrance, Jr. | |
| 4,478,754 A | 10/1984 | Kong-Chan | |
| 4,537,724 A | 8/1985 | McKinnie et al. | |
| 4,587,054 A | 5/1986 | Hardy et al. | |
| 4,588,532 A | 5/1986 | Moyne et al. | |
| 4,634,551 A | * 1/1987 | Burns et al. | ................. 252/102 |
| 4,695,412 A | 9/1987 | Balzer et al. | |
| 4,735,740 A | 4/1988 | Zielske | |
| 4,883,612 A | 11/1989 | Moyne et al. | |
| 5,534,642 A | 7/1996 | Heinzman et al. | |
| 5,650,527 A | 7/1997 | Lutz et al. | |
| 6,218,555 B1 | * 4/2001 | Hembre et al. | ................ 554/99 |

FOREIGN PATENT DOCUMENTS

| | | |
|---|---|---|
| DE | 3824901 | 2/1990 |
| EP | 105672 | 4/1984 |

OTHER PUBLICATIONS

E. J. Bourne et al, Journal of the American Chemical Society. 1949, pp. 2976–2979.*
E. J. Bourne et al, Journal of the Chemical Society. 1954, pp. 2006–2012.*
Chemistry of Organic Fluorine Compounds. 1962, pp. 278–280. Milos Hudlicky.*
Allan H. Gilbert, Detergent Age, 1967, Jun., pp. 18–20.
Allan H. Gilbert, Detergent Age, 1967, Aug., pp. 26–27, 67.
William W. Lowrance, Jr., Tetrahedron Letters, 1971, 37, 3453–54.
Harold R. W. Ansink et al., Recl. Trav. Chim. Pays–Bas, May 1992, 111/5, pp. 215–221.
E. J. Bourne et al., Journal of the Chemical Society, 1949, pp. 2976–2979.
Thomas C. Bruice et al., Journal of American Chemical Society, 1968, 90, pp. 1333–1348.
J. S. Grossert, et al., Canadian Journal of Chemistry, 1981, Sep., vol. 59, No. 17, pp 2617–2620.

* cited by examiner

Primary Examiner—Paul J. Killos
Assistant Examiner—Zachary C. Tucker
(74) Attorney, Agent, or Firm—Michael J. Blake; Bernard J. Graves, Jr.

(57) ABSTRACT

Disclosed is a process for the preparation of aryl carboxylate esters by the reaction of a phenol reactant with a carboxylic acid in the presence of trifluoroacetic acid (TFA) and trifluoroacetic anhydride (TFAA).

12 Claims, No Drawings

PROCESS FOR THE PREPARATION OF ARYL CARBOXYLATE ESTERS

CROSS REFERENCE TO RELATED APPLICATION

This application claims the benefit of U.S. Provisional Application No. 60/153,071, filed Sep. 10, 1999.

INTRODUCTION

This invention pertains to a process for the preparation of aryl carboxylate esters. More specifically, this invention pertains to a process for preparing aryl carboxylate esters by the reaction of a phenol reactant with an carboxylic acid in the presence of trifluoroacetic acid (TFA) and trifluoroacetic anhydride (TFAA).

BACKGROUND OF THE INVENTION

Aryl carboxylate esters such as phenolsulfonate carboxylate esters are useful bleach activators (Allan H. Gilbert, *Detergent Age*, 1967, June, pages 18–20 and August, pages 30–33). Aryl carboxylate esters also are of commercial interest as components of liquid crystals and polyarylate liquid crystal polymers. A number of methods for synthesizing these aryl carboxylate esters are described in the literature. These known procedures, in general, require relatively harsh conditions and proceed slowly to completion. The synthesis of aryl carboxylate esters by boric acid catalysis is described by William W. Lowrance in *Tetrahedron Letters*, 1971, 37, 3453 and in U.S. Pat. No. 3,772,389. The preparation of carboxylate esters by the reaction of an alkanoic acid with a phenolsulfonate salt, e.g., sodium 4-phenolsulfonate (SPS) in the presence of boric acid as described in U.S. Pat. No. 4,478,754 requires many hours at temperatures greater than 180° C. More active carboxylic acid derivatives such as acid chlorides and anhydrides react with SPS under milder conditions. These reactions are carried out either in a solvent or the carboxylic acid related to the desired ester product at temperatures of 80 to 200° C. Esterification of phenolsulfonate salts using carboxylic acid anhydrides as the esterification agent is the preferred route for commercial scale synthesis although other technologies such as aryl carboxylate ester sulfonation described in the literature: Harold R. W. Ansink and Hans Cerfontain, *Recl. Trav. Chim. Pays-Bas*, 1992, 111, 215–21; U.S. Pat. No. 4,695,412.

U.S. Pat. No. 4,587,054 discloses the reaction of a $C_{6-C18}$ carboxylic acid anhydride and substituted phenol at temperatures between 80–120° C. using strong acid catalysis or at temperatures between 180–220° C. using base catalysis. In the examples, the acid-catalyzed process is carried out at 90–100° C. for four hours and the base-catalyzed process is carried out at 200° C. for two hours. Similarly, U.S. Pat. Nos. 4,588,532 and 4,883,612 describe the reaction of a $C_7-C_{12}$ carboxylic acid anhydride in a polar aprotic solvent with SPS in the presence of a catalytic amount of sulfonic acid at temperatures "in excess of about 100° C." An example illustrates the operation of the process at 115 to 120° C. for a period of six hours. U.S. Pat. Nos. 4,588,532 and 4,883,612 also disclose a base-catalyzed process also using a polar aprotic solvent "in excess of 80° C." An example describes a base-catalyzed experiment carried out at 90° C. for three hours. U.S. Pat. No. 5,534,642 discloses the reaction of an amido-substituted carboxylic acid anhydride with a phenolsulfonate salt at 180° C. for 3 hours.

A disadvantage of these known processes wherein carboxylic acid anhydrides are reacted with substituted phenols is that one equivalent of by-product carboxylic acid is produced for each equivalent of the desired aryl carboxylate ester. Thus, processes utilizing anhydrides must recycle the by-product carboxylic acid to be economically attractive. Because the carboxylic acids co-produced in commercial processes typically are high boiling, e.g., $C_6-C_{18}$ carboxylic acids, a simple evaporation of the by-product acid, even at reduced pressure, can require elevated temperatures and associated problems such as formation of color bodies. Likewise, a disadvantage of strong acid-catalyzed processes is the coincident catalysis of desulfonation of the phenolsulonate reactant leading to yield losses and darker colored products.

Procedures for the synthesis of phenolsulfonate alkanoate esters by transesterification, either by alcoholysis or acidolysis, have been published. For example, U.S. Pat. No. 4,537,724 discloses the alcoholysis of phenyl nonanoate with SPS to obtain sodium 4-(nonanoyloxy) benzenesulfonate in 83% yield after heating for four hours at 290–300° C. Alternatively, European Patent Publication EP 105,672 discloses the acidolysis of $C_2-C_3$ alkanoyloxybenzene sulfonates with $C_6-C_{18}$ aliphatic carboxylic (alkanoate) acids, driven by the removal of the lower boiling $C_2-C_3$ acids. In an example, nonanoic acid reacts with acetyloxybenzene sulfonate, using sodium acetate as a catalyst, at 166–218° C. over 3.5 hours. Similarly, U.S. Pat. No. 5,534,642 discloses the acidolysis of acetyloxybenzene sulfonate by amido acids, i.e., alkanoylamido-substituted alkanoic acids, at temperatures of about 200° C. for several hours.

The synthesis of aryl alkanoate esters using an "impeller esterification" technique is known. For example, U.S. Pat. No. 2,082,890 discloses the simultaneous addition of acetic anhydride to a mixture of an alkanoic acid and a phenol to produce the aryl alkanoate ester. An improved impeller method for the synthesis of aryl alkanoate was introduced by E. J. Bourne and coworkers in Journal of the Chemical Society 1949, 2976–79. Bourne et al. disclose the use of TFAA in the synthesis of aryl alkanoate esters using milder conditions. The use of the TFAA impeller esterification method for the synthesis of a phenolsulfonate ester was first disclosed by Thomas C. Bruice et al. in the J.Am.Chem.Soc., 1968, 90, 1333–48. However, the Bruice et al. article does not report a reaction yield, uses an excess of both TFAA and carboxylic acid (relative to the SPS) and employs reaction conditions comparable to those reported by others for strong acid-catalyzed phenolsulfonate ester synthesis. Because TFAA is a relatively expensive chemical, economic considerations discourage its use in large-scale synthesis.

European Patent Publication EP 105,672 discloses the use of acetic anhydride ($Ac_2O$) as an impeller in the preparation of phenolsulfonate alkanoate esters. According to the disclosure of EP 105,672, a $C_2-C_3$ anhydride first is added to a mixture of a phenolsulfonate and $C_6-C_{12}$ carboxylic acid and heated to 140–160° C. and then the temperature is raised so that transesterification (acidolysis) occurs yielding the desired product. Although the reaction conditions are more severe, only one equivalent of nonanoic acid is used, $Ac_2O$ is inexpensive and the reaction yield is high.

The "$Ac_2O$ impeller" method for the synthesis of phenolsulfonate esters also is disclosed in U.S. Pat. Nos. 4,735,740 and 5,650,527 and in German Patent Publication DE 3,824,901 A1. In each of the processes disclosed in these three patent documents, $Ac_2O$ is added to a carboxylic acid of low volatility in the presence of SPS, heated for an extended period of time at relatively high temperatures, e.g., 2–5 hours at temperatures greater than 120° C., and acetic acid is removed at reduced pressure to drive the conversion of SPS to its carboxylic acid ester.

Three disadvantages are inherent to this approach: first, the use of acetic anhydride as an impeller results in a significant amount of acetate ester which must be converted by high temperature transesterification and removal of acetic acid; secondly, not only is transesterification by acidolysis slow, but equilibrium mixtures between acetate esters and other carboxylic esters does not greatly favor the other carboxylic esters and thus the concentration of acetic acid at equilibrium is relatively low; and finally, the low solubility of phenolsulfonate esters in the media employed in these inventions retards reaction progress and is a barrier to clean conversion to the desired products.

BRIEF SUMMARY OF THE INVENTION

I have discovered that when TFA is used as a solvent, or as a major component of the solvent, the reactions of carboxylic acids with phenols impelled by TFAA proceed at unprecedented rates under milder conditions than previously reported. I also have discovered that the use of molar excesses of TFAA is not necessary. This last discovery substantially improves the viability of this method for industrial scale synthesis. The process of the present invention therefore comprise the preparation of aryl carboxylate esters by reacting a phenol with a carboxylic acid containing a total of up to about 24 carbon atoms in the presence of TFA and TFAA wherein the mole ratio of TFAA:phenol is about 3:1 to 0.1:1. Because of the solubility, especially of sodium and potassium phenolsulfonate esters, in TFA, the present invention is especially useful for the preparation of such phenolsulfonate esters. Highly concentrated solutions, e.g., 20–50 weight percent, of these esters can be produced. Such high solubility combined with efficient solvent separation due to the low boiling point of TFA make it uniquely suited to the manufacture of phenolsulfonate esters. Because TFAA impeller esterifications in TFA occur under very mild conditions, the common problem of color formation is not encountered. Likewise, these methods can be applied to the synthesis of a wide variety of phenol esters, including those containing functionality in the carboxylic acid, such as amido acids. For example, the reaction of sodium phenolsulfonate with N-nonanoyl-6-aminocaproic[6-(nonanoylamido)-hexanoic] acid in the presence of TFAA/TFA produces the benzenesulfonate ester in greater than 98% isolated yield in less than 30 minutes at temperatures of from 25 to 45° C. The process of the present invention may be used with difunctional compounds such as dicarboxylic acids, e.g., adipic acid, and/or aromatic diols, e.g., hydroquinone and resorcinol, that are of interest in the preparation of polymeric materials. In most cases, the isolation and purification of products is reduced to simply removing the TFA (b.p. =72° C.) and any excess TFAA (b.p.=40° C.) by evaporation. As mentioned, certain of the carboxylate esters which may be prepared by the present process are useful as bleach activators while others, especially arylene dicarboxylates and diaryl dicarboxylates, are useful in the preparation of polymers. The carboxylate esters also are useful as esterification agents for producing a variety esters.

DETAILED DESCRIPTION

The process of provided by the present invention is a process for the preparation of an aryl carboxylate ester which comprises contacting or reacting a phenol with a carboxylic acid in the presence of TFA and TFAA wherein the mole ratio of TFAA:phenol is about 3:1 to 0.1:1. The phenol reactant may be unsubstituted phenol or naphthol or a hydroxybenzene or hydroxynapthalene compound which may be substituted with a variety of substituents, usually not more than two, such as alkyl of up to about 12 carbon atoms, alkoxy containing up to about 12 carbon atoms, alkanoyl of up to about 12 carbon atoms, halogen such as chloro and bromo, sulfo, an alkali metal salt of sulfo such as sodium and potassium sulfo salts, alkanoylamido containing up to about 20 carbon atoms, nitro, formyl, cyano, alkoxycarbonyl containing 2 to 12 carbon atoms, carbamoyl and the like. The phenol reactant also may be substituted with a second hydroxy group, i.e., 1,2-, 1,3- and 1,4-benzenediols which result in the formation of arylene bis(alkanoate) esters. Additional aromatic diols which may be used include 1,4-naphthalenediol, 4,4'-sulfonyldiphenol and 4,4'-biphenol. The phenol reactant preferably is unsubstituted phenol or an alkali phenolsulfonate, especially sodium phenolsulfonate. The unsubstituted aryl ester produced in accordance with the present invention may be sulfonated to prepare the alkali metal phenolsulfonate ester which are useful as bleach activators.

The carboxylic acid reactant may be an unsubstituted or substituted aliphatic, cycloaliphatic or aromatic carboxylic acid containing a total of up to about 24 carbon atoms. Mixtures of carboxylic acids may be used. The unsubstituted aliphatic acids, preferably unsubstituted alkanoic acids, typically contain 4 to 20, preferably about 6 to 16, carbon atoms. The alkanoic acid, i.e., a saturated, aliphatic carboxylic acid, may be substituted with one or more, typically one, substituent selected from alkoxy containing up to about 12 carbon atoms, halogen such as chloro, alkanoylamido containing up to about 12 carbon atoms, aryl such as phenyl and phenyl substituted with alkyl, alkoxy and/or halogen. The alkanoic acid may be substituted with a second carboxyl group, e.g., adipic acid, azelaic acid and the like, which result in the formation of diaryl dialkanoate esters. The alkanoic acid reactant preferably is an unsubstituted alkanoic acid containing about 6 to 16 carbon atoms or an alkanoic acid containing about 6 to 16 carbon atoms which is substituted with an alkanoylamido group containing up to about 12 carbon atoms. The preferred alkanoic acid reactant includes mixtures containing two or more alkanoic acids containing about 6 to 16 carbon atoms, e.g., a mixture containing approximately 4% hexanoic, 54% octanoic, 39% decanoic and 1% dodecanoic acids.

The carboxylic acid reactant also may be selected from cycloaliphatic and aromatic, carbocyclic, carboxylic acids containing from about 6 to 24 carbon atoms such as cyclohexanecarboxylic acid, benzoic acid, and the naphthalenecarboxylic acids which may be unsubstituted or substituted with a wide variety, usually not more than two, of substituents such as alkyl of up to about 12 carbon atoms, alkoxy containing up to about 12 carbon atoms, alkanoyl of up to about 12 carbon atoms, halogen such as chloro and bromo, sulfo, an alkali metal salt of sulfo such as sodium and potassium sulfo salts, alkanoylamido containing up to about 12 carbon atoms, nitro, formyl, cyano, alkoxycarbonyl containing 2 to 12 carbon atoms, carbamoyl and the like. The cycloaliphatic and aromatic, carbocyclic, carboxylic acids also may be dicarboxylic acids such as 1,2-, 1,3- and 1,4-cyclohexanedicarboxylic acid, 1,2- , 1,3- and 1,4-benzenedicarboxylic acid and the many naphthalenedicarboxylic acid isomers. The carboxylic acid and phenol may be used in carboxylic acid:phenol mole ratios in the range of about 2:1 to 0.5:1, preferably about 1.2:1 to 0.8:1.

TFAA is employed in an amount which gives a TFAA:phenol reactant ratio of about 3:1 to 0.1:1, preferably about 1.5:1 to 0.75:1. This is a feature of the present invention which distinguishes it from known processes which utilize significantly more TFAA. The amount of TFA solvent present initially and during the operation of the process of the present invention typically gives a TFA:phenol reactant mole ratio of at least 0.5:1 and preferably a TFA:phenol mole ratio in the range of about 2:1 to 20:1. Such mole ratios typically provide preferred amounts of TFA greater than 15 weight percent based on the weight of the phenol, carboxylic acid and TFAA present. The amount of TFA present preferably is in the range of about 30 to 80 weight percent based on the weight of the phenol, carboxylic acid and TFAA present. Other inert solvents may be used in conjunction with TFA but are not normally preferred. Examples of such solvents include halogenated hydrocarbons such as dichloromethane and dichlorobenzene; ethers such as diethylether and diglyme; aromatic hydrocarbons such as toluene; and polar aprotic solvents such as dimethylformamide, acetonitrile and sulfolane.

The solvent properties of TFA are unique and highly advantageous in the synthesis of phenolsulfonate esters. Exemplary data showing the solubility of 4-(nonanoyloxy) benzenesulfonate (NOBS) in a series of solvents is displayed in Table 1 wherein solubilities were measured at 23° C. and expressed as grams of NOBS soluble in 100 grams of solution. It is notable that the only solvent in which NOBS is more soluble than water is TFA. I have found no better solvent for NOBS than TFA. This is surprising. First, examination of solvents 2–7 in Table 1 shows a reasonable correlation of NOBS solubility with solvent polarity. TFA is a non-polar solvent with a dielectric constant similar to that of acetic acid yet it dissolves more than ten times the amount of NOBS which is soluble in acetic acid at ambient temperature. It is likely that hydrogen bonding in TFA facilitates the solvation of sulfonate anions but it is notable, in contrast, that such effects are much weaker in acetic acid. Furthermore, while it is known in the art that dimethyl sulfoxide (DMSO) and dimethylformamide (DMF) are relatively good solvents for benzenesulfonate esters they are much weaker solvents than TFA and because TFA has a much lower boiling point than these dipolar aprotic solvents it is the only good solvent for benzenesulfonate esters which can be readily stripped from product solutions and then purified and recycled with relative ease.

TABLE 1

Solubility of NOBS in Selected Solvents

| | wt % NOBS | Dielectric Constant | normal b.p. |
| --- | --- | --- | --- |
| 1. TFA | 23.4 | 8.3 | 71.8 |
| 2. water | 22.8 | 78.3 | 100.0 |
| 3. DMSO | 15.9 | 46.4 | 189.0 |
| 4. DMF | 10.1 | 36.7 | 153.0 |
| 5. NMP | 8.4 | 32.2 | 202.0 |
| 6. acetic acid | 1.7 | 6.2 | 117.9 |
| 7. nonanoic acid | 0.03 | 1.7 | 254.0 |
| 8. acetone | 0.02 | 20.6 | 56.1 |
| 9. acetonitrile | 0.01 | 35.9 | 81.6 |

In Table 1, the dielectric constants and boiling points were taken from Christian Reichardt *Solvent and Solvent Effects in Organic Chemistry*; VCH: Weinheim, 1988; *Trifluoroacetic Acid*, by John B. Milne In *Chemistry of Non-Aqueous Solvents*, Vol 5B; J. J. Lagowski, Ed.; Academic Press: New York, 1978; pages 1–52 and G. Geisler and E. Manz *Monat. Chem.* 1969, 100, 1133–39. NMP is N-methylpyrrolidinone.

An important advantage of the present invention is that the novel esterification process may be carried out at relatively low temperature, e.g., temperatures in the range of about −10 to 80° C., which results in improved selectivity to the desired product of higher quality due to the avoidance or minimization of the formation of color bodies. However, if desired, the process may be carried out over a broad range of temperatures, e.g., temperatures of about −50 to 250° C. Pressure is not an important aspect of the present invention and, thus, the process may be carried out at pressures moderately above or below ambient temperature.

A further advantage of the present invention is its applicability not only to a wide variety of carboxylic acids but also to mixtures of carboxylic acids. Because fatty acids (especially from natural sources) are often obtained as mixtures of carboxylic acids, the ability to convert such a mixture to its corresponding mixture of benzenesulfonate esters offers a great advantage to a manufacturer that wishes to utilize such low cost feedstocks. For example, a mixture of alkanoic carboxylic acids known as C-810 is available from Procter & Gamble Chemicals. This mixture contains about 4% hexanoic, 54% octanoic, 39% decanoic and 1% dodecanoic acids. As described above, TFA is readily removed by evaporation under mild conditions so purification of the products to high purity white powders is vastly simplified in contrast to processes described in the art which rely on crystallization and filtration to purify benzenesulfonate esters. Such methods, when applied to a mixture of benzenesulfonate esters, are complicated by variable rates of crystallization that exist for different benzenesulfonate ester products. The embodiment of the present invention is readily applied to the manufacture of products containing a mixture of benzenesulfonate esters.

The process may be carried out as a batch process or in a continuous or semi-continuous mode of operation. Batch operation is illustrated in the examples presented herein. In continuous operation of the process, a mixture of carboxylic acid(s) and a phenol in TFA are treated with TFAA in an esterification reactor that is appropriately agitated so that the initial slurry is well mixed. With adequate time in the esterification reactor a solution is produced which can be, for instance in the case of benzenesulfonate esters, spray-dried to remove nearly all TFA, e.g., >95%. The solid product may be further dried of TFA by, for instance, a fluidized-bed drier which can reduce the residual TFA in solid products to significantly less than 1%. Such solid products typically are very white (L>90 on the Hunter Lab color scale).

EXAMPLES

The process provided by the present invention is further illustrated by the following examples. The following abbreviations used in the examples: TFA=trifluoroacetic acid, TFAA=trifluoroacetic anhydride, TBAH=tetrabutylammonium hydrogen sulfate, SPS=sodium phenolsulfonate, o-SPS=sodium ortho-phenolsulfonate, NOBS=sodium 4-(nonanoyloxy)benzene sulfonate, NACOBS=sodium 6-(nonanoylamido)caproyloxybenzene sulfonate, $C_n$OBS=the benzenesulfonate ester of a normal carboxylic acid with n carbons and NACA=6-(nonanoylamido)caproic acid.

The spray dryer used was an APV Anhydro Model Lab 1 spray dryer, 1 meter (39 inches) in diameter and 1.83 meters (6 feet) tall with a conical bottom. Nitrogen was used as the drying gas at a flow of 0.68 kg (1.5 pounds) per hour and velocity of 38.1 meters (125 feet) per second (based on the orifice size and pressure drop). The inlet temperature was set at 185–195° C., the outlet temperature was 90–100° C. and the spray rate was 40 g per minute. Atomization was counter-current using a two-fluid nozzle with a 1.5 mm (0.060 inch) fluid orifice and a (0.25 mm (0.010 inch) opening for the atomizing gas (nitrogen). The nozzle is located approximately at the mid-point of the dryer chamber. The solids were separated by a cyclone and the exhaust gas bubbled through a caustic bath to scrub TFA vapors. Depending on batch size, yield from the dryer was 70 to 85%. Control experiments demonstrate that no benzenesulfonate ester hydrolysis occurs during this process and that from 2–5 weight percent TFA remains in the white powders produced by this treatment.

All NMR spectra were obtained on a Varian Gemini 300 NMR spectrometer with samples dissolved in $d_6$-DMSO, unless otherwise indicated. Chemical shifts (δ) are referenced to residual protons in DMSO at 2.50 ppm and the carbon signal of DMSO at 39.51 ppm. Procedures are not optimized with respect to yields, which are reported relative to the conversion of SPS.

Gas chromatography was used to analyze fatty acids and was carried out on an HP 5890 GC with flame ionization detection using a DB-5 column (0.25 μ, 30 m×0.32 mm). The nonanoic acid used obtained from and found to be 97.4% pure including 2.2% of 2-methyloctanoic acid. The $C_{8/10}$ carboxylic acid mixture used was found to contain hexanoic acid (3.8 wt %), octanoic acid (54.0 wt %), decanoic acid (38.7 wt %) and dodecanoic acid (0.5%).

The 6-(nonanoylamido)caproic acid (NACA) was recrystallized twice from methanol to obtain flaky, white crystalline material. It was shown by LC analysis to be 99.9% pure with 0.1 weight percent caprolactam as the only impurity. Liquid chromatography was performed on an HP 1100 instrument using a Keystone Scientific Betasil C18 column (5μ, 150 mm×4.6 mm) and UV/Vis detection (λ=220; $\lambda_{ref}$= 370 nm). In general, 0.1–0.5 g of sample (depending on purity) was dissolved in 50 ml of 85:15 water:acetonitrile. Tetrabutylammonium hydrogensulfate (TBAH, $5\times10^{-3}$ M) adjusted to a pH of 2.1 with phosphoric acid was used as eluent. Different benzenesulfonate esters were resolved using specific solvent gradient profiles. The SPS used was analyzed by the same LC method and found to contain p-SPS (>95%), o-SPS (<2%) and 4,4'-diphenylsulfone (<0.2%) in addition to water (2.4%) determined by the Karl Fischer method.

Trace contents of TFA were quantified by hydrolysis/ capillary electrophoresis (CZ) using a Beckman-Coulter P/ACE MDQ capillary electrophoresis unit with indirect UV detection using λ=240 nm.

Reflectance color of product ("whiteness") is quantified by CIELAB, i.e. the Hunter L*,a*,b*, scale in which L is a measure of "lightness" (0=black, 100 =white). A HunterLab D25M Optical Sensor with HunterLab DP-9000 Processor was used for these measurements.

Example 1

A 3.0 L three-neck roundbottom flask with a Friedrich condenser, a mechanical stirrer and a pressure-equalized dropping addition funnel was flushed with nitrogen for ten minutes. Nonanoic acid (158.85 g, 1.00 moles), SPS (203.29 g, 1.01 moles) and TFA (768.17 g) were placed in the flask and the resulting slurry stirred at ambient temperature under nitrogen. TFAA (302.16 g, 1.44 moles) was placed in the dropping addition funnel, then added in a single rapid addition. The reaction solution warmed to 45–56 C. and was stirred for ten minutes. Further TFAA additions (total of 30 ml., 0.211 moles) were made to reach a point where very little solid remained in the stirred reaction solution. These white solids were filtered and the homogeneous solution weighed (1428.2 g, 96.7% of theoretical). A sample of this solution (21.01 g) was withdrawn and evaporated to a dry white solid (5.21 g) under reduced pressure. Analysis of this material by liquid chromatography, cz analysis for TFA, and Karl Fischer analysis for water are consistent with a 99.0% reaction yield and a mass balance of 99.8%.

The remaining homogeneous solution was spray-dried and then heated to 500° C. for six hours in a vacuum oven at ~10 mm pressure. This powder measured by liquid chromatography contained 97.1% NOBS and 2.3% 2-Me-$C_8$OBS, consistent with the analysis of the carboxylic acid reactant described above. CZ analysis showed <1% TFA, Karl Fischer analysis <0.2% water in this powder and its whiteness, measured by the Hunter Lab method, corresponded to an L* value of 91.8.

$^1$H and $^{13}$C NMR show complete are consistent with the above analyses: $^1$H NMR (DMSO-$d_6$): $^1$H NMR: δ 7.63, d (8.3, 2H), 7.05, d (8.2, 2H), 2.56, t (7.4, 2H), 1.63, m (2H), 1.27 (10 H), 0.86, t (3H). $^{13}$C NMR: δ 171.7, 150.4, 126.9, 121.0, 33.4, 31.2, 28.7, 28.5, 28.4, 24.3, 22.1 and 14.0 ppm.

Example 2

A 300 ml, round-bottom flask with a nitrogen inlet and a magnetic stir bar was flushed with nitrogen for ten minutes. Nonanoic acid (4.45 g, 28.0 millimoles—mmol), sodium phenolsulfonate (5.00 g, 25.0 mmol) and TFA were placed in the flask which was sealed with a septum cap and the resulting slurry was stirred while being cooled by an ice-water bath. A single rapid addition of TFAA (6.5 ml) was made via syringe. Within one minute the slurry is dissolved to yield a homogeneous solution. The stirring was continued for five minutes. The volatiles were removed by rotary evaporation yielding a white solid that was washed with 100 ml of acetone and collected on a Buchner funnel. The resulting white solid was dried under reduced pressure yielding 7.90 g (94% yield) of sodium 4-(nonanoyloxy) benzene-sulfonate (NOBS). $^1$H and $^{13}$C NMR show complete conversion of the SPS to NOBS.

Example 3

In the same manner as in Example 2, 3.45 g of hexanoic acid (29 mmol) and 5.35 g of SPS (27 mmol) in 30 ml of TFA were reacted in the presence of 6.5 ml of TFAA, yielding 7.19 g of product (91% yield) determined to be sodium 4-(hexanoyloxy)benzenesulfonate ($C_6$-OBS) by NMR. $^1$H NMR: δ 7.62, d (8.8, 2H); 7.04, d (8.5, 2H); 2.58, t (7.4, 2H); 1.65, m (2H); 1.35 (4H) and 0.90, t (3H). $^{13}$C NMR: δ 171.8, 150.4, 145.9, 126.8, 121.0, 33.4, 30.6, 24.0, 21.8 and 13.8 ppm.

Example 4

In the same manner as in Example 2, 4.64 g of octanoic acid (32 mmol) and 5.71 g of SPS (29 mmol) in 30 ml TFA were reacted in the presence of 7.0 ml of TFAA, yielding 8.30 g of product (88% yield) determined to be sodium 4-(octanoyloxy)benzenesulfonate ($C_8$-OBS) by NMR. $^1$H NMR: δ 7.61, d (8.8, 2H); 7.05, d (8.7, 2H); 2.57, t (7.1, 2H); 1.64, m (2H); 1.37 (8H) and 0.87, t (3H). $^{13}$C NMR: δ 171.8, 150.4, 126.9, 121.1, 33.5, 31.1, 28.4, 24.4, 22.1 and 14.0 ppm.

Example 5

In the same manner as in Example 2, 5.00 g of decanoic acid (29 mmol) and 5.24 g of SPS (27 mmol) in 30 ml TFA were reacted in the presence of 6.5 ml of TFAA, yielding 8.29 g of product (88% yield) determined to be sodium 4-(decanoyloxy)benzenesulfonate ($C_{10}$-OBS) by NMR. $^1$H NMR: δ 7.62, d (8.5, 2H); 7.05, d (8.7, 2H); 2.56, t (7.5, 2H); 1.63, m (2H); 1.26 (14H) and 0.86, t (3H). $^{13}$C NMR: δ 171.8, 150.5, 145.8, 126.9, 121.1, 33.5, 31.3, 28.9, 28.74, 28.70, 28.43, 28.36, 22.2 and 14.0 ppm.

Example 6

In the same manner as in Example 2, 6.21 g of lauric acid (31 mmol) and 5.71 g of SPS (29 mmol) in 40 ml TFA were reacted in the presence of 7.0 ml of TFAA, yielding 8.30 g of product (88% yield) determined to be sodium 4-(lauroyloxy)benzenesulfonate ($C_{12}$-OBS) by NMR. $^1$H NMR: δ 7.62, d (8.8, 2H); 2.57, t (9.0, 2H); 1.63, m (2H); 1.26 (16 H) and 0.86, t, Hz (3H). $^{13}$C NMR: δ 171.8, 150.4, 126.9, 121.1, 33.5, 31.3, 29.0, 28.9, 28.7, 28.7, 28.4, 24.3, 22.1 and 14.0 ppm.

Example 7

In the same manner as in Example 2, 4.94 g (31 mmol) of 2-methyl-octanoic acid and 5.58 g (29 mmol) in 30 ml TFA of SPS were reacted in the presence of 7.0 ml of TFAA, yielding 9.26 g of product (88% yield) determined to be sodium 4-(2-methyloctanoyloxy)benzenesulfonate (2MO-OBS) by NMR. $^1$H NMR: δ 7.63, d (8.8, 2H); 7.03, d (8.8, 2H); 2.69, q (6.0, 2H); 1.63, m (2H); 1.70, m (2H); 1.53, m (2H); 1.28 (6H); 1.21, d (6.8, 16 H) and 0.88, t, (3H). $^{13}$C NMR: δ 174.7, 150.3, 146.0, 126.8, 120.9, 33.5, 31.1, 28.6, 26.5, 22.0, 16.7 and 13.9 ppm.

Example 8

Using the same apparatus and procedure described in Example 1 101.4 g (0.65 moles) of $C_{810}$-acid (composed of a mixture of $C_6$, $C_8$, $C_{10}$ and $C_{12}$ acids, as described above) and 131.4 g of SPS (0.64 moles) in 481.9 g of TFA were treated with 167.5 g of TFAA (0.80 moles) and the solution stirred for twenty minutes at 23–45° C. At that point the slurry had become essentially homogeneous and was filtered through a 40-mesh wire filter. Analysis of a sample of the product solution was consistent with a 99.0% reaction yield and a mass balance of 99.8%. The spray-dried powder following further vacuum drying (~10 mm) at 50° C. for six hours was shown by liquid chromatography to contain $C_6$OBS (5.6%), $C_8$OBS (56.2%), $C_{10}$OBS (35.5%) and $C_{12}$OBS (0.4%) which thus account for 97.7% product purity and corresponds well to the analysis of the $C_{810}$ mixture of carboxylic acids (97.0%) used as the starting material. CZ analysis showed <1% TFA, Karl Fischer analysis <0.25% water in this powder and its whiteness, measured by the Hunter Lab method, corresponded to an L* value of 91.7.

Example 9

Using the same apparatus and procedure described in Example 1, 244.2 g (1.00 moles) of NACA (99.9%) and 169.4 g of SPS (1.00 moles) in 1864.9 g of TFA were treated with 232.4 g of TFAA (1.11 moles) and the solution stirred for ten minutes at 23–50° C. At that point the slurry had become essentially homogeneous and was filtered through a 40-mesh wire filter. Analysis of a sample of this product solution was consistent with a 99.5% reaction yield and a mass balance of 100.5%. The spray-dried powder following further vacuum drying (~10 mm) at 50° C. for six hours was shown by liquid chromatography to contain NAC-OBS (99.5%) containing 0.04% NOBS. CZ analysis showed <1% TFA, Karl Fischer analysis <0.15% water in this powder and its whiteness, measured by the Hunter Lab method, corresponded to an L* value of 93.5.

NMR analyses are consistent with the above analyses: $^1$H NMR (DMSO-$d_6$): $^1$H NMR: δ 7.76, t (6, 1H); 7.61, d (8.2, 2H); 7.04, d (8.3, 2H); 3.03, t (6, 2H); 2.56, t (2H); 1.63, m (2H); 1.5–1.3 m (6H); 1.23 (10 H); 0.85, (3H). $^{13}$C NMR: δ 171.9, 171.7, 150.3, 146.0, 126.8, 121.0, 38.1, 35.1, 33.4, 31.2, 28.8, 28.7, 28.65, 28.62, 25.8, 25.3, 24.1, 22.1, 14.0 ppm.

Example 10

A 300 ml roundbottom flask with a sidearm attached to nitrogen and a magnetic stir bar was flushed with nitrogen for ten minutes. N-Nonanoyl-6-aminocaproic acid (NACA, 12.61 g, 46 mmol), SPS (8.34 g, 42 mmol) and TFA (75 ml) were placed in the flask which was sealed with a septum cap and the resulting slurry stirred while being cooled by an ice-water bath. Rapid addition of TFAA (6.0 ml) was made via syringe. After five minutes a sample was withdrawn and assayed by NMR for reaction progress. A second injection of trifluoroacetic anhydride was then made (7.0 ml). After five minutes the reaction slurry was converted to a homogeneous solution. The volatiles were removed by rotary evaporation and 100 ml of acetone was added to yield a white solid that was collected on a Buchner funnel. This was dried under reduced pressure at 500° C. for an hour yielding 17.91 g of product (95% yield). $^1$H and $^{13}$C NMR show complete conversion of the SPS to sodium 4-(N-nonanoyl-6-aminocaproyloxy)benzenesulfonate (NACA-OBS).

Example 11

4,4'-Sulfonyidiphenol (18.15 g, 72.5 mmol), octanoic acid (23.15 g, 160 mmol) and 55 ml of TFA were placed in a 300 ml two-neck flask with an argon inlet and a septum cap. While the flask was cooled by an ice-water bath TFAA (42 ml, 296 mmol) was added rapidly by syringe. After thirty minutes at 0° C. the reaction mixture became nearly homogeneous. The volatiles were stripped, the residue dissolved in 100 ml of methylene chloride and washed with saturated aqueous sodium bicarbonate solution (3×100 ml). The organic layer was dried over magnesium sulfate, filtered through paper, and the volatiles were stripped on a rotary evaporator yielding 30.99 g of product (85% yield) determined to be 4,4'-sulfonyidiphenylsulfonyl bis(octanoate) by NMR. In the same manner the diesters of 4,4'-disulfonylphenol were prepared with hexanoic, decanoic and dodecanoic acids. The IR spectra of each of the sulfone diesters in cyclohexane contain bands for the carbonyl of the esters at 1774 cm$^{-1}$ and of the $SO_2$ group at 1157 cm$^{-1}$.

NMR characterization of these derivatives is reported below. $^1$H NMR (CDCl$_3$): δ 7.96 (d, 6.6, 4H), 7.25 (d, 8.8, 4H), 2.57 (t, 8.2, 4H), 1.74 (m, 4H); $^{13}$C NMR (CDCl$_3$): δ 171.8, 154.7, 138.6, 129.6, 122.8, 34.5, 31.8, 29.2 29.1, 25.0, 22.8, 1.30 (m, 4H), 0.89 (m, 6H) 14.3 ppm.

Example 12

The procedure described in Example 11 was repeated except that the octanoic acid was replaced 6.95 g of hexanoic acid (59.5 mmol) and an appropriate amount of disulfonylphenol (6.90 g, 27.5 mmol) to obtain 11.1 g (90% yield) of 4,4'-sulfonyidiphenylsulfonyl bis(hexanoate). $^1$H NMR (CDCl$_3$): δ 7.96 (d, 8.9, 4H), 7.24 (d, 8.9, 4H), 2.57 (t, 7.7, 2H), 1.75 (m, 2H); $^{13}$C NMR (CDCl$_3$): δ 171.6, 154.7, 138.7, 129.6, 122.8, 34.5, 31.4, 24.6, 22.5, 14.1 ppm.

Example 13

The procedure described in Example 11 was repeated except that the octanoic acid was replaced with 10.64 g of decanoic acid (61.8 mmol) and an appropriate amount of 4,4'-sulfonyidiphenol (6.88 g, 27.5 mmol) to obtain 13.7 g (89% yield) of 4,4'-sulfonyldiphenylsulfonyl bis (decanoate). $^1$H NMR (CDCl$_3$): δ 7.96 (d, 6.6, 4H), 7.25 (d, 8.8, 4H), 2.57 (t, 8.2, 4H), 1.74 (m, 4H); $^{13}$C NMR (CDCl$_3$): δ 170.7, 153.9, 137.7, 128.6, 122.1, 33.5, 31.1, 28.6, 28.4, 28.2, 24.0, 1.30 (m, 4H), 0.89 (m, 6H) 21.9, 13.5 ppm.

Example 14

The procedure described in Example 11 was repeated except that the octanoic acid was replaced with 13.46 g of dodecanoic acid (67.2 mmol) and an appropriate amount of 4,4'-sulfonyidiphenol (8.42 g, 33.6 mmol) to obtain 18.0 g (87% yield) of 4,4'-sulfonyldiphenylsulfonyl bis (dodecanoate). $^1$H NMR (CDCl$_3$): δ 7.96 (d, 8.9, 4H), 7.24 (d, 8.9, 4H), 2.57 (t, 7.7, 2H), 1.75 (m, 2H); $^{13}$C NMR (CDCl$_3$): δ171.5, 154.6, 138.6, 129.5, 122.7, 34.4, 32.0, 29.7, 29.5, 29.4, 29.3, 1.38 (m, 4H), 0.92 (t, 7.1, 6H) 29.1, 24.9, 22.8, 14.2 ppm.

Example 15 p-Nitrophenol (2.94 g, 21 mmol), nonanoic acid (3.70 g, 23 mmol) and 10 ml of TFA were placed in a 300 ml two-neck flask with an argon inlet and a septum cap. While the flask was cooled by an ice-water bath TFAA (6.5 ml, 45.8 mmol) was added rapidly by syringe. After ten minutes at 0° C. the reaction mixture has become homogeneous. The volatiles were stripped yielding 4.86 g of crude product (83% yield) determined to be p-nitrophenyl nonanoate by NMR. $^1$H NMR (CDCl$_3$): δ 8.33, m (2H); 7.33, m (2H); 2.66, t (7.7, 2H); 1.82, m (2H); 1.36 m (16H) and 0.89, m (4H). $^{13}$C NMR (CDCl$_3$): δ 171.9, 155.7, 145.4, 125.4, 122.6, 34.5, 32.0, 29.34, 29.26, 29.22, 24.9, 22.8 and 14.3 ppm.

Example 16 p-Hydroquinone (2.08 g, 18.9 mmol), p-toluic acid (5.67 g, 41.6 mmol) and 20 ml of TFA were placed in a 300 ml two-neck flask with an argon inlet and a septum cap. While the flask was cooled by an ice-water bath TFAA (12 ml, 84.6 mmol) was added rapidly by syringe. After twenty minutes at 0° C. and then warmed to 23° C. for ten minutes before stripping the volatiles on a rotary evaporator to yield 6.88 g of crude product (110%). Analysis by NMR is consistent with the expected product, 1,4-bis(p-toluoyloxy)benzene. $^1$H NMR (CDCl$_3$): δ 8.11, d (8.2, 4H); 7.33, d (4H); 7.28, s (4H) and 2.47, s (6H). $^{13}$NMR (CDCl$_3$): δ 165.4, 148.6, 144.7, 130.4, 129.5, 126.8, 122.9 and 22.0 ppm Example 17

In the same manner as in Example 5, 3.0 of 2-isobutyric acid (34 mmol) and 5.94 g of SPS (30 mmol) in 30 ml TFA were reacted in the presence of 7.0 ml of TFAA, yielding 6.81 g of product (85% yield) determined to be sodium 4-(isobutyroyloxy)benzenesulfonate (i-C$_4$-OBS) by NMR. $^1$H NMR: δ 7.62, d (8.8, 2H); 7.05, d (8.8, 2H); 2.81, h (6.9, 1H) and 1.22, d (6.9, 6H). C NMR: δ 175.0, 150.5, 126.9, 120.9, 33.3 and 18.7 ppm.

Example 18

In the same manner as in Example 5, 3.24 g of pivalic acid (32 mmol) and 5.54 g of SPS (28 mmol) in 35 ml of TFA were reacted in the presence of 7.0 ml of TFAA , yielding 8.20 g of product (91% yield) determined to be sodium 4-(pivaloyloxy)benzenesulfonate (Piv-OBS) by NMR: δ $^1$H NMR: δ 7.62, d (8.8, 2H); 7.02, d (8.8, 2H) and 1.30 (9H). $^{13}$C NMR: δ 172.0, 151.1, 145.7, 127.1, 121.6, 30.9 and 26.9 ppm.

Example 19

In the same manner as in Example 5, 1.97 g of adipic acid (31 mmol) and 5.54 g of SPS (29 mmol) in 40 ml of TFA were reacted with 12.8 ml of TFAA, yielding 6.60 g of product (97% yield) determined to be bis(4-sodium sulfophenyl) adipate (Adip-OBS) by NMR. $^1$H NMR: δ 7.62, d (8.8, 2H); 7.05, d (8.8, 2H); 2.65, m (4H) and 1.73, m (4H). $^{13}$C NMR: δ 171.6, 150.3, 126.9, 121.0, 33.1 and 23.7 ppm.

Example 20

In the same manner as in Example 5, 5.08 g of p-toluic acid (37 mmol) and 6.71 g of SPS (34 mmol) were reacted in the presence of 10.0 ml of TFAA and 50 ml TFA. After two minutes a slurry still exists but after fifteen minutes at 0° C. the reaction mixture has become nearly homogeneous. The volatiles were stripped and the residue washed with 100 ml of acetone and dried on a rotary evaporator yielding 14.00 g of product (100% yield) determined to be sodium 4-(p-toluoyloxy)benzenesulfonate (PTA-OBS) by NMR. $^1$H NMR: δ 8.03, d (8.0, 2H); 7.68, d (8.5, 2H); 7.41, d (8.2, 2H); 7.22, d (8.5, 2H) and 2.42, m (4H). $^{13}$C NMR: δ 164.6, 150.6, 146.1, 144.6, 129.9, 129.6, 127.0, 126.1, 121.2 and 21.3 ppm.

Example 21

In the same manner as in Example 5, 6.20 g of methacrylic acid (72.0 mmol) and 12.84 g of SPS (65.4 mmol) were reacted in the presence of 50 ml of TFA and 22.0 ml of TFAA. After fifteen minutes at 0the mixture was allowed to warm to 23° C. and stirred for fourteen hours under argon. During this time it became homogeneous. The volatiles were stripped and the residue washed with 100 ml of acetone and dried on a rotary evaporator yielding 21.8 g of product (126% yield) determined to be sodium 4-(methacryloxy) benzenesulfonate (MA-OBS) by NMR. $^1$H NMR: δ 7.64, d (8.5, 2H); 7.11, d (8.5, 2H); 6.28, br s (1 H); 5.90, br s (1 H) and 2.00, s (3H). $^{13}$C NMR: δ 165.3, 150.5, 146.0, 135.2, 127.8, 126.9, 121.0 and 18.0 ppm.

Example 22

In the same manner as in Example 5, 5.51 g of crotonic acid (64.0 mmol) and 9.86 of SPS (50.2 mmol) were reacted in the presence of 100 ml of TFA and 18.0 ml of TFAA. After two minutes the initial slurry became nearly homogeneous so it was allowed to stir for an additional ten minutes at 0° C. The volatiles were stripped and the residue dried on a rotary evaporator yielding 14.6 g of product (87% yield) determined to be sodium 4-(crotonyloxy)benzenesulfonate (CROT-OBS) by NMR. $^1$H NMR: δ 7.63, d (8.5, 2H); 7.14, dd (15.4, 6.9; 1H); 7.08, d (8.2, 2H); 6.13, dd (15.6, 1.65; 1H) and 1.94, d (6.9, 3H). $^{13}$C NMR: δ 164.2, 150.4, 148.1, 145.8, 126.9, 121.4, 121.1 and 18.0 ppm.

Example 23

In the same manner as in Example 5, 1.41 g of nonanoic acid (8.9 mmol) and 2.43 g of disodium 2,4-disulfonatophenol (8.12 mmol) were reacted in the presence of 2.60 ml of TFAA and 10 ml TFA. After fifteen minutes at 0° C. the slurry was warmed to 23° C. and stirred for 12 hours. The volatiles were stripped and $^1$H NMR revealed about 50% conversion of disulfonated phenol to its nonanoate ester. A second treatment with 2.60 ml of TFAA and 10 ml of TFA for thirty minutes at 23° C. resulted in a near-homogeneous solution which, following the removal of volatiles by evaporation and washing the white solids with 100 ml acetone, yielded 2.86 g of product (80% yield) determined to be sodium nonanoyloxy-2,4-benzene-disulfonate by $^1$H and $^{13}$C NMR. $^1$H NMR: δ 8 8.02, d (2.2, 1H); 7.54, dd (8.2, 2.2; 1H); 7.43, d (8.2, 1H); 2.47, t (7.7, 2H); 1.60, m (2H); 1.27, m (10H) and 0.86, t (6.8, 3H). $^{13}$C NMR: δ 171.3, 147.0, 145.0, 139.1, 126.7, 126.1, 123.1, 33.6, 31.2, 28.8, 28.6, 28.5, 24.0, 22.1 and 14.0 ppm.

Example 24

In the same manner as in Example 5, 4.61 g of nonanoic acid (29.1 mmol) and 6.38 g of sodium 3-nitro-4-hydroxybenzenesulfonate (26.4 mmol) were reacted in the presence of 30 ml TFA and 8.30 ml of TFAA at 0° C. for fifteen minutes. The slurry was then warmed to 23° C. and stirred for 12 hours. $^1$H NMR assay of a sample showed 80% conversion to the desired ester so an additional 2 ml of TFAA was added to the reaction and it was stirred for an additional hour. The volatiles were stripped and washing yellow solids with 100 ml acetone, yielded 4.75 g of product (47% yield) determined to be sodium nonanoyloxy-2-nitro4-benzenesulfonate by $^1$H and $^{13}$C NMR. $^1$H NMR: δ 8.22, d (1.7, 1H); 7.98, dd (8.5, 2.0, 1H); 7.43, d (8.2, 1H); 2.63, t (7.4, 2H); 1.64, m (2H); 1.26, m (10H) and 0.85, t (6.8, 3H). $^{13}$C NMR: δ 171.0, 147.1, 143.0, 140.7, 132.2, 125.2, 122.4, 33.2, 31.2, 28.6, 28.5, 28.3, 24.0, 22.1 and 14.0 ppm.

The invention has been described in detail with particular reference to preferred embodiments thereof, but it will be understood that variations and modifications can be effected within the spirit and scope of the invention.

I claim:

1. A process for the preparation of an aryl carboxylate ester which comprises reacting a phenol with a carboxylic acid in the presence of trifluoroacetic acid (TFA) and trifluoroacetic anhydride (TFAA) wherein the mole ratio of TFAA:phenol reactant is about 3:1 to 0.1:1 and the amount of TFA present initially and during the operation of the process gives a TFA:phenol reactant mole ratio of about 2:1 to 20:1.

2. A process according to claim 1 wherein the carboxylic acid reactant is an aliphatic, cycloaliphatic or aromatic carboxylic acids containing a total of up to about 24 carbon atoms and the carboxylic acid:phenol mole ratio is about 2:1 to 0.5:1.

3. A process for the preparation of an aryl carboxylate ester which comprises reacting a phenol with a carboxylic acid in the presence of trifluoroacetic acid (TFA) and trifluoroacetic anhydride (TFAA) wherein the mole ratio of TFAA:phenol reactant is about 3:1 to 0.1:1; the amount of TFA present initially and during the process gives a TFA:phenol reactant mole ratio of at least about 2:1; the phenol reactant is phenol, a hydroxybenzene sulfonic acid or an alkali hydroxybenzenesulfonate; and the carboxylic acid reactant is an unsubstituted alkanoic acid containing about 8 to 16 carbon atoms or an alkanoic acid containing about 6 to 16 carbon atoms substituted with an alkanoylamido group containing up to about 12 carbon atoms.

4. A process according to claim 3 wherein the process is carried out at a temperature of about −10 to 80° C. and the carboxylic acid:phenol mole ratio is about 2:1 to 0.5:1.

5. A process according to claim 4 wherein the amount of TFAA present gives a TFAA:phenol reactant ratio of about 1.5:1 to 0.75:1 and the amount of TFA present initially and during the operation of the process gives a TFA:phenol reactant mole ratio of about 2:1 to 20:1.

6. A process according to claim 5 wherein the phenol reactant is phenol, a hydroxybenzenesulfonic acid, a sodium hydroxybenzene-sulfonate or a potassium hydroxybenzenesulfonate; and the carboxylic acid reactant is an unsubstituted alkanoic acid containing about 6 to 20 carbon atoms.

7. A process according to claim 5 wherein the phenol reactant is phenol, a hydroxybenzene sulfonic acid or a sodium hydroxybenzene-sulfonate or a potassium hydroxybenzenesulfonate; and the carboxylic acid reactant is an alkanoic acid containing about 6 to 20 carbon atoms substituted with an alkanoylamido group containing up to about 12 carbon atoms.

8. A process for the preparation of a mixture of aryl carboxylate esters which comprises reacting a phenol with a mixture of carboxylic acids in the presence of trifluoroacetic acid (TFA) and trifluoroacetic anhydride (TFAA) wherein the mole ratio of TFAA:phenol reactant is about 3:1 to 0.1:1; the amount of TFA present initially and during the process gives a TFA:phenol reactant mole ratio of at least about 2:1; the phenol reactant is phenol, a hydroxybenzene sulfonic acid or an alkali hydroxybenzenesulfonate; and the mixture of carboxylic acids is composed of carboxylic acids selected from unsubstituted alkanoic acids containing about 6 to 16 carbon atoms or alkanoic acids containing about 6 to 16 carbon atoms substituted with an alkanoylamido group containing up to about 8 to 16 carbon atoms.

9. A process according to claim 8 wherein the process is carried out at a temperature of about −10 to 80° C. and the total moles of carboxylic acid:phenol mole ratio is about 2:1 to 0.5:1.

10. A process according to claim 9 wherein the amount of TFAA present gives a TFAA:phenol reactant ratio of about 1.5:1 to 0.75:1 and the amount of TFA present initially and during the operation of the process gives a TFA:phenol reactant mole ratio of about 2:1 to 20:1.

11. A process according to claim 10 wherein the phenol reactant is phenol, a hydroxybenzenesulfonic acid, a sodium hydroxybenzene-sulfonate or a potassium hydroxybenzenesulfonate; and the mixture of carboxylic acids comprises two or more carboxylic acids selected from unsubstituted alkanoic acids containing about 6 to 20 carbon atoms.

12. A process according to claim 10 wherein the phenol reactant is phenol, a hydroxybenzene sulfonic acid or a sodium hydroxybenzene-sulfonate or a potassium hydroxybenzenesulfonate; and the mixture of carboxylic acids comprises two or more carboxylic acids selected from alkanoic acids containing about 6 to 20 carbon atoms substituted with alkanoylamido groups containing about 8 to 16 carbon atoms.

* * * * *